US00PP37585P3

(12) United States Plant Patent
Olesen

(10) Patent No.: US PP37,585 P3
(45) Date of Patent: Aug. 18, 2026

(54) MINIATURE ROSE PLANT NAMED 'Poulpah127'

(50) Latin Name: *Rosa hybrida*
Varietal Denomination: Poulpah127

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/831,800

(22) Filed: Sep. 15, 2025

(65) Prior Publication Data

US 2026/0114338 P1 Apr. 23, 2026

(30) Foreign Application Priority Data

Sep. 19, 2024 (QZ) ..... PBR 20242186

(51) Int. Cl.
*A01H 5/02* (2018.01)
*A01H 6/74* (2018.01)

(52) U.S. Cl.
USPC ..... Plt./122
CPC ..... *A01H 6/749* (2018.05); *A01H 5/02* (2013.01)

(58) Field of Classification Search
USPC ..... Plt./122, 129, 150, 151
CPC . A01H 5/02; A01H 5/00; A01H 6/749; A01H 6/74
See application file for complete search history.

(56) References Cited

U.S. PATENT DOCUMENTS

PP24,090 P3 * 12/2013 Olesen ..... A01H 5/02 Plt./122

OTHER PUBLICATIONS

CPVO Application Consultation Version 4.25.4 for Poulpah127 retrieved on Feb. 4, 2026 at https://online.plantvarieties.eu/publicConsultationDetails?registerId=20242186&denomination=poulpah127, 2 pp. (Year: 2026).*

* cited by examiner

*Primary Examiner* — June Hwu

(57) ABSTRACT

A new garden rose plant of the Miniature class which has abundant, red flowers and attractive foliage. This new and distinct variety has shown to be uniform and stable in the resulting generations from asexual propagation.

2 Drawing Sheets

Botanical designation: *Rosa hybrida.*
Variety denomination: 'Poulpah127'.

This application claims priority to Plant Breeder's Rights Application Number 2024/2186, which was filed at the Community Plant Variety Rights Office in the European Union on Sep. 19, 2024, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2015 and the resulting seeds were planted in a controlled environment in Fredensborg, Denmark. The new variety, named 'Poulpah127', originated as a single seedling from the stated cross The new variety may be distinguished from its male pollen parent and female seed parent by the following characteristics. The male pollen parent plant has red flowers with no scent, while the new variety has red flowers with a moderate clove like scent. The female seed parent plant has a flower tonality of Red Group 53A, while the new variety has a flower tonality of Red Group 45A. The female seed parent has smaller flowers, 55 mm, compared to 'Poulpah127' which has a flower diameter of 65 mm.

The objective of the hybridization of this rose variety was to create a new and distinct variety with unique qualities, such as:

1. Uniform and abundant red flowers with long shelf-life;
2. Vigorous, but compact growth when propagated on its own roots;
3. Suitability for production in containers; and
4. Exceptional disease resistance.

This combination of qualities is not present in previously available commercial cultivars of this type, known to the inventor, and distinguish 'Poulpah127' from all other varieties of which we are aware.

As part of the rose development program, Mogens N. Olesen germinated the seeds from the aforementioned hybridization during winter of 2015 and conducted evaluations on the resulting seedlings in a controlled environment in Odense, Denmark. 'Poulpah127' was selected in the spring of 2016 by the inventor as a single plant from the progeny of the aforementioned hybridization.

Asexual reproduction of 'Poulpah127' by rooted cuttings was first done by Mogens N. Olesen in the nursery in Odense, Denmark in July 2016. This initial and other subsequent asexual propagations conducted in controlled environments have demonstrated that the characteristics of 'Poulpah127' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah127'.

Specifically illustrated in FIG. 1 of the drawings are open flowers viewed from above and the side, flower petals detached revealing reproductive flower parts, sepals detached, a partially opened flower, and flower buds.

Figure 1:
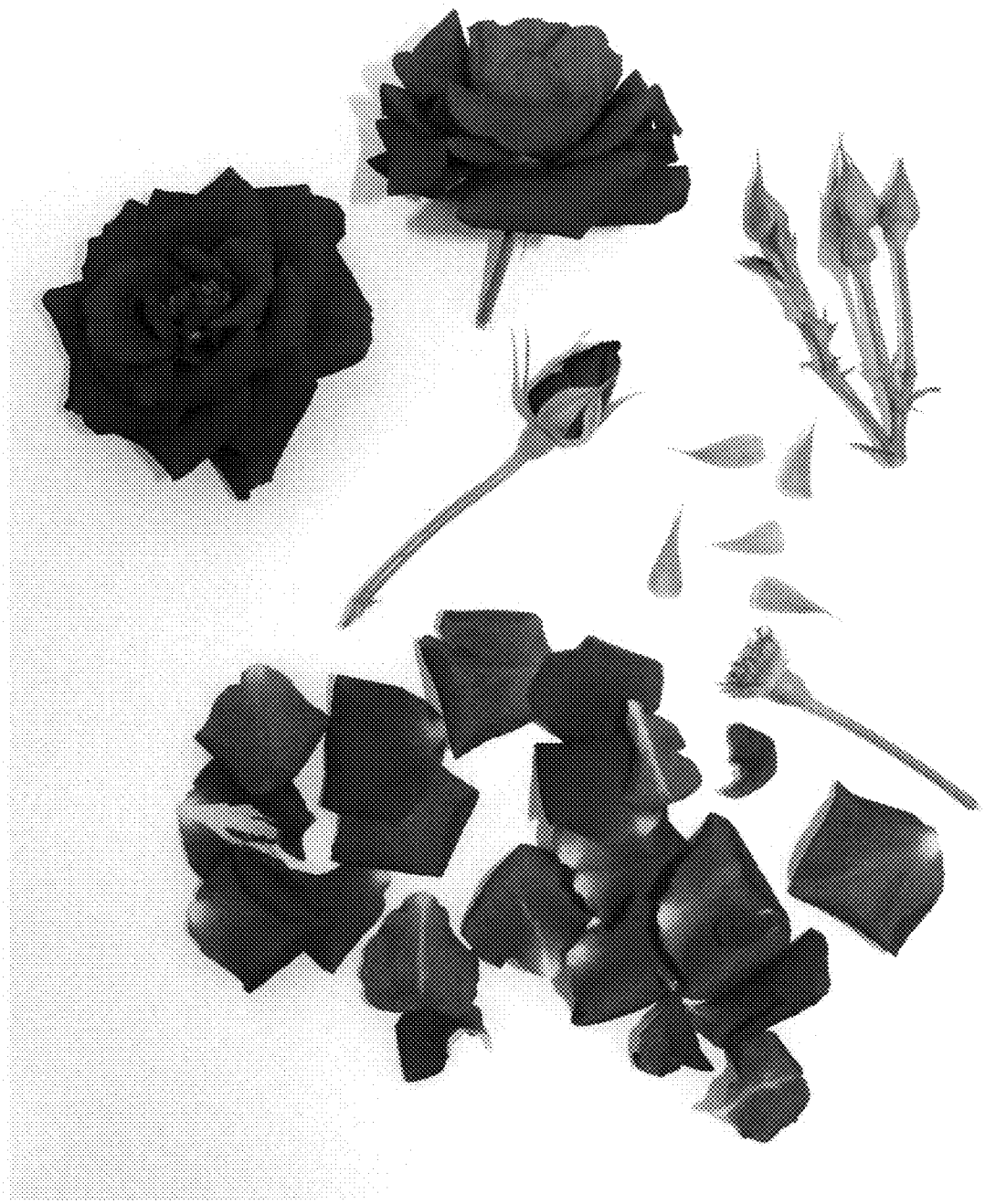
Figure 2:
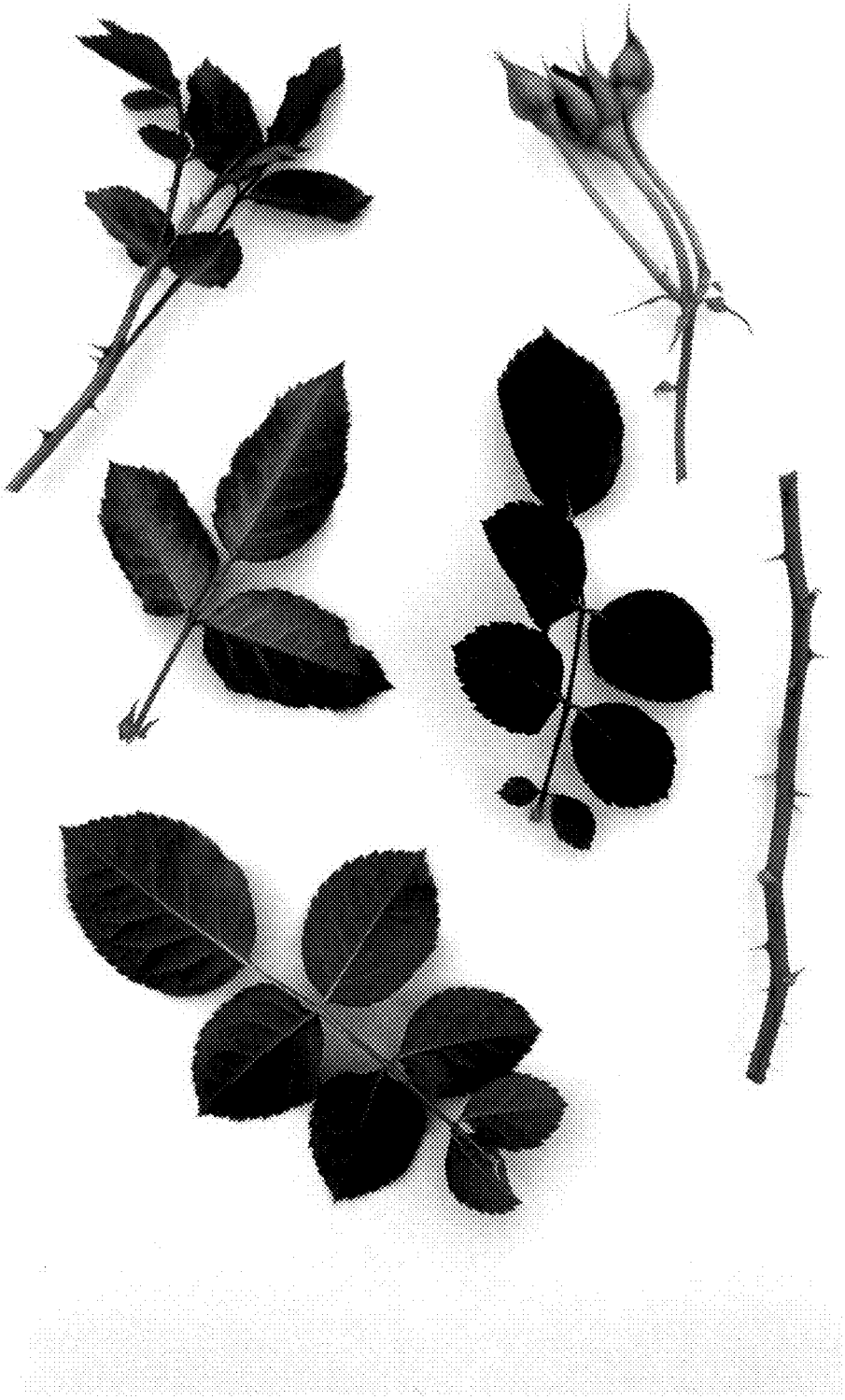

Specifically illustrated in FIG. 2 of the drawings are mature leaves, juvenile leaves exhibiting anthocyanin, a bare stem with prickles, and a cluster of flower buds.

Plants shown are 3 months old.

DETAILED DESCRIPTION OF THE VARIETY

The following is a description of 'Poulpah127', as observed in its growth in a glasshouse nursery in Odense Denmark. Observed plants are 3 months of age, and were grown on their own roots in 17 cm pots. Color references are made using The Royal Horticultural Society (London, England) Colour Chart, 2001, except where common terms of color are used.

For a comparison, several physical characteristics of the rose variety 'Poulpah053', U.S. Plant Pat. No. 24,090 are compared to the claimed plant. While 'Poulpah127' has 22 flower petals, 'Poulpah053' has about 30 flower petals. The claimed plant has a flower diameter of 65 mm while 'Poulpah053' has a flower diameter of 45 mm. Open flowers of 'Poulpah127' are generally Red Group 45B in color while 'Poulpah053' has a general tonality of Red Group 53B.

Flower and Flower Bud

Blooming habit: Continuous.

Flower bud:

- *Size*.—Upon opening, 30 mm in length from base of receptacle to end of bud. Bud diameter is 13 mm.
- *Bud form*.—Urceolate.
- *Bud color*.—As sepals divide petals are Red Group 46A.
- *Sepal inner surface*.—Color: Yellow-Green Group 145A and 145B. Surface: Lightly pubescent.
- *Sepal outer surface*.—Color: Yellow-Green Group 144A. Texture: Rough with fragrant stipitate glands.
- *Sepal shape*.—Apex: Cirrhose. Base: Flat at union with receptacle.
- *Sepal margin*.—Margins have moderate foliaceous appendages on three of the five sepals.
- *Sepal size*.—26 mm long, 9 mm wide.
- *Receptacle*.—Texture: Smooth. Size: 7 mm in height, 6 mm wide. Color: Yellow-Green Group 144A. Shape: Campanulate.
- *Pedicel*.—Surface: Rough with stipitate glands. Length: 30 to 50 mm. Diameter: 2.5 mm on average. Color: Yellow-Green Group 144A. Strength: Strong.
- *Peduncle*.—Length: 1 to 2 cm. Diameter: About 4 mm. Color: Yellow-Green Group 144A. Texture: Smooth.

Flower bud development: Flower buds are borne in clusters of 3 to 4 flower buds per stem. Development as a corymb.

Flower bloom:

- *Fragrance*.—Moderate clove like scent.
- *Duration*.—The blooms have a duration on the plant of approximately 25 days. Petals fall cleanly away from plant after flowers have fully matured.
- *Size*.—Flower diameter is 65 mm when open. Flower depth is 35 mm.
- *Flower shape*.—Rosette, double flower with slightly overlapping petals of different sizes.
- *Shape of flower, side view*.—The upper portion is convex. The lower portion is concave.

Petalage: Under normal conditions, flowers have about 22 petals.

General tonality of flower: Open flowers are Red Group 45B.

Petal color:

- *Upon opening, outer petals*.—Upper surface: Red Group 45A. Occasionally streaks Green-White Group 157D. Lower surface: Red Group 53B and C.
- *Upon opening, inner petals*.—Upper surface: Red Group 45A with occasional streaks Green-White Group 157D. Lower surface: Red Group 53B and C.
- *Basal petal spots, upon opening*.—Upper surface: Yellow Group 7C. Lower surface: Yellow Group 4B.
- *After opening, inner and outer petals*.—Upper surface: Red Group 45A with occasional streaks Green-White Group 157D. Lower surface: Red Group 53B.
- *Basal petal spots, after opening*.—Upper surface: Yellow Group 7C. Lower surface: Yellow Group 4B.

Petals:

- *Petal reflex*.—Partially reflexed.
- *Margin*.—Entire and uniform with moderate undulations.
- *Shape*.—Broad and elliptic. Apex shape: Rounded. Base shape: Acute.
- *Size*.—38 mm (1) x 44 mm (w).
- *Texture*.—Smooth.
- *Thickness*.—Average.

Petaloids:

- *Size*.—21 mm (1) by 13 mm (w).
- *Quantity*.—About 4.
- *Shape*.—Elliptical with an acute base and rounded apices.
- *Color*.—The upper surface is Red Group 45A. Lower surface Red Group 53B.

Reproductive flower parts:

- *Pollen*.—None observed.
- *Anthers*.—Size: 1 mm in length. Color: Greyed-Orange Group 163A. Quantity: 55 on average.
- *Filaments*.—Color: Yellow Group 7A with intonations of Orange-Red Group 32B. Length: 9 mm.
- *Pistils*.—Length: 6 mm. Quantity: 35 on average.
- *Stigmas*.—Color: Orange-White Group 159A.
- *Styles*.—Color: Green-White Group 157A with intonations of Red-Purple Group 62C.
- *Hips*.—None Observed.

Plant

Plant growth: Upright. Plants are 37 cm in height, and 28 cm wide.

Stems:

- *Color of juvenile growth*.—Yellow-Green Group 144B.
- *Color of mature growth*.—Yellow-Green Group 144A.

*Length*.—Canes are about 19 cm from the base of the plant to the flowering portion.

*Diameter*.—About 4 mm.

*Internodes*.—On mature canes about 30 mm between nodes.

*Surface texture*.—Young wood: Smooth. Older wood: Smooth.

Long prickles:

*Incidence*.—About 12 prickles per 10 cm of stem.

*Size*.—Average length of prickles on mature stems is 6 mm.

*Shape*.—Upper portion is linear. Lower portion is linear.

*Color*.—Juvenile prickles: Greyed-Red Group 180B. Mature prickles: Greyed-Yellow Group 160B.

Plant foliage:

*Compound leaf*.—125 mm (1) x 130 (w).

*Quantity*.—3 leaves per 10 cm of stem on average.

*Leaf bearing angle to the stem*.—90 to 100 degrees.

*Color of juvenile foliage*.—Upper side: Yellow-Green Group 144B with intonations of Greyed-Purple Group 183B. Lower side: Yellow-Green Group 144B.

*Color of mature foliage*.—Upper side: Yellow-Green Group 146A. Lower side: Yellow-Green Group 147B.

Plant leaves and leaflets:

*Stipules*.—Size: 6 mm long, 2 mm wide. Quantity: 2 per compound leaf. Shape: Linear, slightly broad based with outward extending apices. Margins: Finely serrated. Color: Yellow-Green Group 144A.

*Petiole*.—Length: On average 13 mm. Diameter: 2 mm. Upper surface color: Yellow-Green Group 144A. Lower surface color: Yellow-Green Group 144A.

*Rachis*.—Length: About 70 mm. Upper surface color: Yellow-Green Group 144A with intonations of Greyed-Purple Group 183A. Lower surface color: Yellow-Green Group 144A.

*Leaflet*.—Quantity: Normally 5 to 7 leaflets. Margins: Serrated. Size: Terminal leaflets are about 55 mm long, 30 mm wide. Shape: Generally elliptical. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae,* downy mildew *Peronospora sparsa,* rust *Phragmidium* spp., black spot *Diplocarpon rosae,* and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpah127' substantially as described and illustrated herein.

* * * * *